US011286527B2

(12) United States Patent
Mikko et al.

(10) Patent No.: US 11,286,527 B2
(45) Date of Patent: Mar. 29, 2022

(54) DIAGNOSTIC TEST FOR SKELETAL ATAVISM IN HORSES

(71) Applicants: Sofia Mikko, Knivsta (SE); Leif Andersson, Uppsala (SE); Gabriella Lindgren, Knivsta (SE); Carl-Johan Rubin, Uppsala (SE); Bhanu Chowdhary, College Station, TX (US); Terje Raudsepp, College Station, TX (US); Evan E. Eichler, Seattle, WA (US); John Huddleston, Seattle, WA (US); Maika Malig, Seattle, WA (US)

(72) Inventors: Sofia Mikko, Knivsta (SE); Leif Andersson, Uppsala (SE); Gabriella Lindgren, Knivsta (SE); Carl-Johan Rubin, Uppsala (SE); Bhanu Chowdhary, College Station, TX (US); Terje Raudsepp, College Station, TX (US); Evan E. Eichler, Seattle, WA (US); John Huddleston, Seattle, WA (US); Maika Malig, Seattle, WA (US)

(73) Assignees: CAPILET GENETICS AB, Vasteras (SE); UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 16/004,537

(22) Filed: Jun. 11, 2018

(65) Prior Publication Data

US 2018/0282812 A1 Oct. 4, 2018

Related U.S. Application Data

(63) Continuation of application No. 14/888,994, filed as application No. PCT/US2014/036746 on May 5, 2014, now abandoned.

(30) Foreign Application Priority Data

May 6, 2013 (SE) .................................. 1330047-0

(51) Int. Cl.
*C07H 21/04* (2006.01)
*C12Q 1/68* (2018.01)
*A01K 67/00* (2006.01)
*C12Q 1/6883* (2018.01)

(52) U.S. Cl.
CPC ..... *C12Q 1/6883* (2013.01); *C12Q 2600/156* (2013.01)

(58) Field of Classification Search
None
See application file for complete search history.

(56) References Cited

U.S. PATENT DOCUMENTS 7,208,274 B2   4/2007  Dhallon
2003/0059805 A1 3/2003  Rappold

OTHER PUBLICATIONS

Lear et al. (Sex Dev. vol. 6, pp. 61-71, Nov. 17, 2011). (Year: 2011).*
Raudsepp et al. (Cytogeneti Genome Res, vol. 121, No. 2, pp. 102-109, 2008.*
Tyson, "Skeletal Atavism in a minature horse," Veterinary Radiology & Ultrasound, Jul. 1, 2004, vol. 45, pp. 315-317.
Shears, "Mutation and detection of the pseudoautosomal gene SHOX cause Leri-Weill dyschodrosteosis," Nature Genetics, May 1, 1998, vol. 19, pp. 7-73.
Leka, "Short stature and sysmorphology associated with defects in the SHOX gene," Homones, Apr. 1, 2006, vol. 5, pp. 107-118.
International Search Report issued in PCT/US2014/036746, dated Sep. 20, 2014, pp. 1-3.
Written Opinion issued in PCT/US2014/036746, dated Sep. 30, 2014, pp. 1-10.
Extended European Search Report issued in EP application No. 14794101.7, dated Dec. 12, 2016, pp. 1-8.
Sara Benito-Sanz, "A Novel class of pseudoautosomal region 1 deletions downstream of SHOX is associated with Leri-Weill Dyschondrosteosis," The American Journal of Human Genetic, Jan. 1, 2005, pp. 533-544.
Flanagan, "Prevelance of mutations in the short stature homeobox containing gene SHOX in madelung deformity of childhood," Journal of Medical Genetics, vol. 39, No. 10, Oct. 1, 2002, pp. 758-763.
Blaschke, "The pseudoautosomal regions, SHOX and disease," Current Opinion in Genetics & Development, Current Biology Ltd., XX, vol. 16, No. 3, Jun. 1, 2006, pp. 233-239.
Beate, "The human SHOX mutation database," Human Mutation, vol. 20, No. 5, Nov. 25, 2002, pp. 338-341.
Lear et al. (Sex Dev. vol. 6, pp. 61-71, Nov. 17, 2011).
Raudsepp et al. (Cytogenet. Genome Res. vol. 121, pp. 102-109, 2008).
Speed, "A cause of malformation of the limbs of shetland ponies with a note on its phylogenic significance," The British Veterinary Journal, 1958:18-22.
Hermans, "A hereditary anomaly in shetland ponies," Neth J. vet. Sci. 1970, 3(1): 55-63.
Shamis, "Complete ulnas and fibulas in a pony foal," J. Am. Vet. Med Assoc. 1985, 186:802-804.
Tyson, "Skeletal atavism in a minature horse," Vet. Radiol Ultrasound 2004, 45:315-317.

(Continued)

*Primary Examiner* — Jeanine A Goldberg
(74) *Attorney, Agent, or Firm* — Jeffrey S. Melcher; Melcher Patent Law PLLC

(57) ABSTRACT

The present invention relates to methods for detecting a genetic deletion at the SHOX locus of a horse, where the presence of such a genetic deletion indicates that the horse is a carrier of disease-causing mutation that can lead to skeletal atavism. The invention further provides nucleic acid primers and probes for use in methods for detecting the presence or absence of disease-causing genetic deletion at the SHOX locus of a horse.

3 Claims, 1 Drawing Sheet

Specification includes a Sequence Listing.

(56) References Cited

OTHER PUBLICATIONS

Wade, "Genome sequence, comparative analysis, and population genetics of the domestic horse," Science 2009, 326:865-867.
Durbin, "Fast and accurate short read alignment with Burrows-Wheeler trasform," Bioninformantics 2009, 25:1754-1760.
Handsaker, "The sequence alignment/map format and SAMtools," Bionformantics 2009, 25:2078-2079.
McKenna, "The genome analysis tookit: a MapReduce framework for analyzing next-generation DNA sequencing data," Genome Res 2010, 20:1297-1303.
Blashke, "The pseudoautosomal regions, SHOX and disease," Curr Opin. Genet. Dev 2006, 16:233-239.
Rosilio, "Genotypes and phenotypes of children with SHOX deficiency in France," J. Clin Endocrinol Metab 2012, 97:E1275-1265.

\* cited by examiner

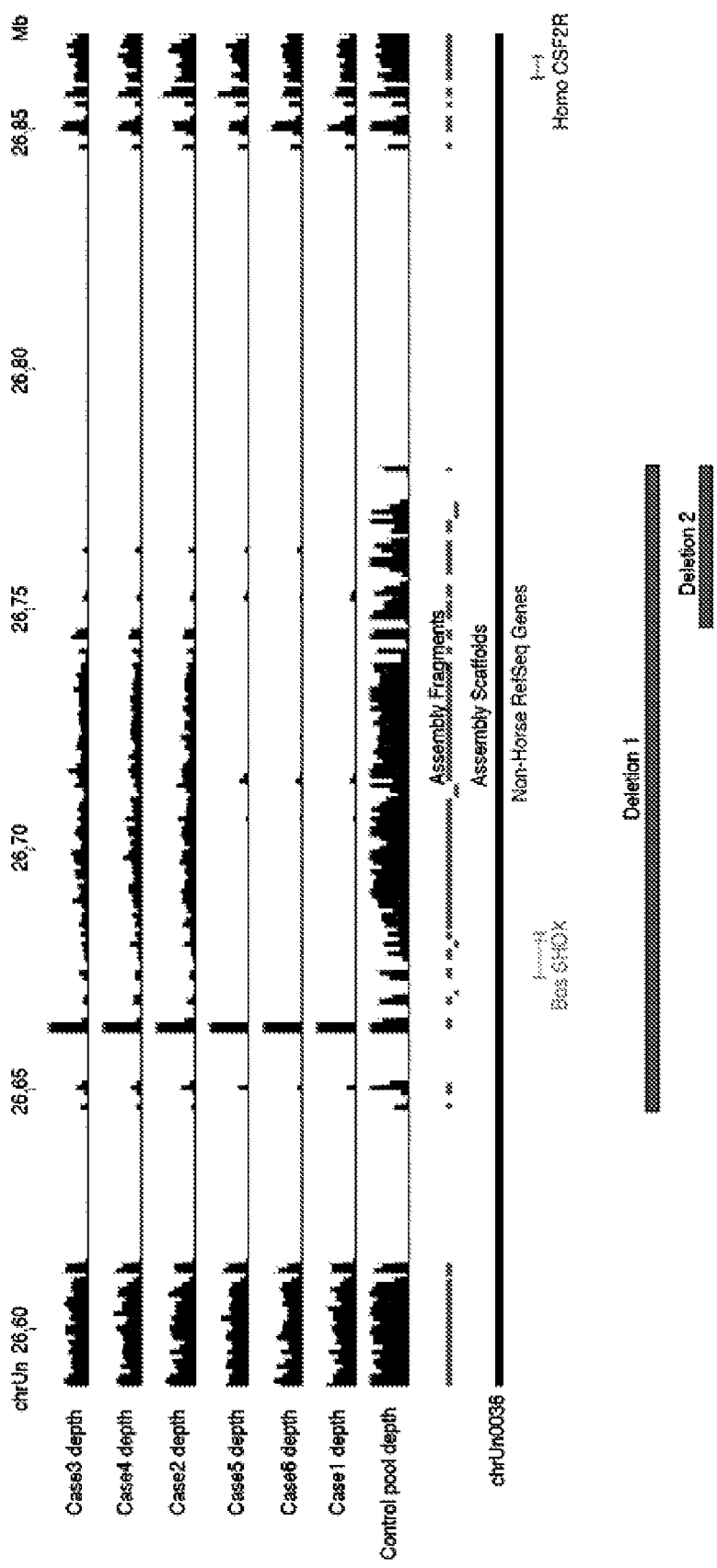

DIAGNOSTIC TEST FOR SKELETAL ATAVISM IN HORSES

FIELD OF THE INVENTION

The present invention relates to methods and nucleic acid fragments for detecting a genetic deletion at the SHOX locus of a horse, where the presence of such a genetic deletion indicates that the horse is a carrier of disease-causing mutation that can lead to skeletal atavism.

BACKGROUND OF THE INVENTION

Speed [1] and Hermans [2] published the first scientific reports on fully developed ulna and fibula in horses, and they both described this defect in the Shetland pony breed. Speed described this anatomic variation as a type of atavism in certain families of Shetland pony foals in the United Kingdom. The affected foals had complete ulnas and fibulas with associated angular limb deformities and developed progressive interrupted movements and lameness. The recurrence in certain families suggested a hereditary basis for the anomaly. Speed described that the parents were phenotypically normal and the anomaly was noted to skip generations. Hermans (1970) reported that fifty Shetland ponies with atavism were recorded in Utrecht from year 1961 to 1967. Hermans performed test matings to elucidate the inheritance pattern of the defect and the results suggested that skeletal atavism in Shetland ponies follow an autosomal recessive mode of inheritance.
In addition to Shetland ponies rare occurrences of the defect have been described in Welsh pony [3] and in Miniature horse [4].

There is a strong need in the horse breeding industry to develop a diagnostic test to identify animals that are carriers of the recessive allele causing skeletal atavism so that such carriers can be eliminated from the breeding population which means that the disorder will be eradicated.

DESCRIPTION OF THE INVENTION

The present inventors have identified mutations that can lead to skeletal atavism in the horse. The mutations are demonstrated to be two different deletion alleles, D1 and D2, associated with the Short Stature Homeobox (SHOX) locus.

Accordingly, the present invention provides methods for detecting disease-causing genetic deletions at the SHOX locus of a horse, where the presence of such a genetic deletion indicates that the horse is a carrier of a mutation that can lead to skeletal atavism.

Put another way, the present invention provides methods for determining if a horse is a carrier of a mutation that can lead to skeletal atavism. The method can comprise the steps,
  i) extracting DNA from a sample obtained from a horse,
  ii) determining in said DNA the presence of a genetic deletion at the SHOX locus,
  where the presence of said genetic deletion indicates that the horse is a carrier of a mutation that can lead to skeletal atavism.

The genetic deletion can be the D1 and/or the D2 deletion according to the present invention. The horse carrying a disease-causing mutation can be heterozygous for the D1 allele, the D2 allele, or both the D1 and D2 alleles, or homozygous for the D1 allele or the D2 allele.

The D1 allele is the allele with the D1 genetic deletion, the D2 allele is the allele with the D2 deletion.

In one aspect, the present invention provides methods for detecting the presence of a nucleic acid sequence in the genome of a horse, said nucleic acid sequence being a part of the D1 deletion. Preferably, the nucleic acid sequence to be detected can be selected from a nucleic acid sequence present in the nucleic acid sequences SEQ ID NOs: 10 to 117.

The presence of one copy only of said nucleic acid in the genome of said horse, being indicative of said horse being heterozygous for the D1 deletion, and hence a carrier of a disease-causing mutation than can lead to skeletal atavism. The absence of said nucleic acid in the genome of said horse, being indicative of said horse being homozygous for the D1 deletion, and hence a carrier of a disease-causing mutation that can lead to skeletal atavism.

The D1 deletion according to the invention comprises the contigs indicated in Table 2 of the horse reference genome assembly EquCab2 corresponding to SEQ ID NOs: 10 to 110.

The D1 deletion according to the invention comprises the nucleic acid sequences present in the BAC derived contigs indicated in Table 5 corresponding to SEQ ID NOs: 111 to 117.

In another aspect, the present invention provides methods for detecting the presence of a nucleic acid sequence in the genome of a horse, said nucleic acid sequence being a part of the D2 deletion. Preferably, the nucleic acid sequence to be detected can be selected from a nucleic acid sequence present in the nucleic acid sequences SEQ ID NOs: 10 to 58, 91 to 95, 97 to 110, and 115 to 117.

The presence of one copy only of said nucleic acid in the genome of said horse, being indicative of said horse being heterozygous for the D2 deletion, and hence a carrier of a disease-causing mutation that can lead to skeletal atavism. The absence of said nucleic acid in the genome of said horse, being indicative of said horse being homozygous for the D2 deletion, and hence a carrier of a disease-causing mutation that can lead to skeletal atavism.

The D2 deletion according to the invention comprises the nucleic acid sequences present in the contigs indicated in Table 2 of the horse reference genome assembly EquCab2 corresponding to SEQ ID NOs: 10 to 58, 91 to 95, and 97 to 110.

The D2 deletion according to the invention comprises the nucleic acid sequences present in the BAC derived contigs indicated in Table 5 corresponding to SEQ ID NOs: 115 to 117.

The term "SHOX locus" is intended to include all DNA sequences of the BAC derived contigs of the horse genome listed in Table 5, i.e. the DNA sequences corresponding to SEQ NOs:111 to 117, and any intervening DNA sequences, including 100 kB upstream and downstream of the SHOX gene.

"Sketetal Atavism" refers to the disorder involving ulna and fibula development in the horse, as the condition to some extent mimics the skeletal development present in ancestors of horses with full development of the ulna and tibia.

According to one aspect of the invention the methods according to the present invention can be used for selecting horses for breeding.

According to one aspect of the invention the methods according to the present invention can be used for parental testing of horses.

Preferably, the methods according to the invention comprise extraction of DNA from a biological sample obtained from a horse.

The term "sample" or "biological sample" according to the present invention refers to any material containing nucleated cells from said horse to be tested. In a preferred embodiment the biological sample to be used in the methods of the present invention is selected from the group consisting of blood, sperm, hair roots, milk, body fluids as well as tissues including nucleated cells.

DNA extraction, isolation and purification methods are well-known in the art and can be applied in the present invention. Standard protocols for the isolation of genomic DNA are inter alia referred to in Sambrook, J., Russell. D. W. Molecular Cloning: A Laboratory Manual, the third edition, Cold Spring Harbor Laboratory Press, Cold Spring Harbor. New York, 1.31-1.38, 2001 and Sharma. R. C., et al. "A rapid procedure for isolation of RNA-free genomic DNA from mammalian cells", BioTechniques, 14. 176-178, 1993.

There are several methods known by those skilled in the art for determining whether a particular nucleotide sequence is present in a DNA sample and for identifying the nucleotide in a specific position in a DNA sequence. These include the amplification of a DNA segment encompassing the genetic marker by means of the polymerase chain reaction (PCR) or any other amplification method, interrogate the genetic marker by means of allele specific hybridization, the 3'exonuclease assay (Taqman assay), fluorescent dye and quenching agent-based PCR assay, the use of allele-specific restriction enzymes (RFLP-based techniques), direct sequencing, the oligonucleotide ligation assay (OLA), pyrosequencing, the invader assay, minisequencing, DHPLC-based techniques, single strand conformational polymorphism (SSCP), allele-specific PCR, denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (YRS), microarrays, a rolling circle extension assay, HPLC-based techniques, extension based assays, ARMS (Amplification Refractory Mutation System), ALEX (Amplification Refractory Mutation Linear Extension), SBCE (Single base chain extension), molecular beacon assays, invader (Third wave technologies), ligase chain reaction assays, 5'-nuclease assay-based techniques, hybridization capillary array electrophoresis (CAE), single molecule sequencing such as nanopore sequencing, protein truncation assays (PTT), immunoassays, and solid phase hybridization (dot blot, reverse dot blot, chips). This list of methods is not meant to be exclusive, but just to illustrate the diversity of available methods. Some of these methods can be performed in accordance with the methods of the present invention in microarray format (microchips) or on beads.

The invention thus also relates to primers, primer pairs or probes, hybridizing under stringent conditions to a nucleic acid sequence present in or flanking the deleted regions D1 and D2 according to the invention, or to the complementary strand thereof, and their use in the methods according to the invention. By a nucleic acid sequence flanking the deleted regions D1 and D2 is meant nucleic acid sequences 10 kB upstream or downstream of D1 or D2, such as 1 kB, or 100 bases upstream or downstream of D1 or D2.

Primers hybridizing to these flanking regions are particularly useful for PCR amplification in the methods according to the invention. Use of one primer hybridizing to a nucleic acid sequence in D1 and one primer hybridizing to a nucleic acid sequence flanking the D1 will only lead to amplification when D1 is present. Use of one primer hybridizing to a nucleic acid sequence in D2 and one primer hybridizing to a nucleic acid sequence flanking the D2 will only lead to amplification when D2 is present. Use of one primer hybridizing to a nucleic acid sequence flanking D1 upstream and one primer hybridizing to a nucleic acid sequence flanking D1 downstream will only lead to amplification when D1 is absent. Use of one primer hybridizing to a nucleic acid sequence flanking D2 upstream and one primer hybridizing to a nucleic acid sequence flanking D2 downstream will only lead to amplification when D2 is absent.

Primers hybridizing to nucleic acid sequences introduced by a mutational event leading to and creating D1 and/or D2 are particularly useful for PCR amplification in the methods according to the invention.

Preferably the primers or primer pairs hybridize(s) under stringent conditions to the sequences SEQ ID NOs: 10 to 110, or to the complementary strand thereof.

Preferably, the primers of the invention have a length of at least 14 nucleotides such as 17 or 21 nucleotides.

More specifically the primers can be selected from SEQ NO:1, SEQ ID NO:2, SEQ ID NO:3, SEQ ID NO:4, SEQ ID NO:5, and SEQ ID NO:6.

Hybridization is preferably performed under stringent or highly stringent conditions. "Stringent or highly stringent conditions" of hybridization are well known to or can be established by the person skilled in the art according to conventional protocols. Appropriate stringent conditions for each sequence may be established on the basis of well-known parameters such as temperature, composition of the nucleic acid molecules, salt conditions etc.: see, for example, Sambrook et al. "Molecular Cloning, A Laboratory Manual", CSH Press, Cold Spring Harbor, 1989 or Higgins and Hames (eds.), "Nucleic acid hybridization, a practical approach", IRL Press, Oxford 1985, see in particular the chapter "Hybridization Strategy" by Britten & Davidson. Typical (highly stringent) conditions comprise hybridization at 65° C. in 0.5×SSC and 0.1% SDS or hybridization at 42° C. in 50% formamide, 4×SSC and 0.1% SDS. Hybridization is usually followed by washing to remove unspecific signals. Washing conditions include conditions such as 65° C., 0.2×SSC and 0.1% SDS or 2×SSC and 0.1% SDS or 0.3×SSC and 0.1% SDS at 25° C.-65° C.

LEGEND TO FIGURES

FIG. 1: Depth of sequence read coverage observed in whole genome resequencing. Shown is the depth at the SHOX locus for six Skeletal Atavism cases (CG1-6) and for the pool of healthy control stallions. Boxes have been inserted to visualize approximate locations of the two deletions in the EquCab2 assembly context.

EXAMPLES

Methods
Illumina Sequencing and Sequence Analysis

DNA samples from six Shetland ponies diagnosed by veterinarians with Skeletal Atavism (SA), individuals CG1, CG2, CG3, CG4, CG5 and CG6, as well as a control pool consisting of equimolar amounts of DNA from 22 stallions (who had never fathered Atavistic foals despite having fathered many foals) were prepared for sequencing. Illumina paired-end libraries were generated from these DNA samples with mean insert sizes of approximately 220 bp. The two libraries were sequenced using an Illumina HiSeq instrument as paired-end reads (2×100 bp). The reads were mapped to the horse reference genome assembly [5] using the software BWA [6], and PCR-duplicates were removed using the software Picard (http://picard.sourceforge.net). The average read depth obtained was approximately 7× for each SA individual and approximately 55× average depth for the control pool. SNPs and small insertions/deletions were called from the mapping data after subjecting the alignments to realignment around indels and then variant calling using the Genome Analysis Toolkit (GATK) [8]. The variant calls were subjected to recommended VariantFiltrationWalker filters for SNPs listed in the GATK wiki page (http://www.broadinstitute.org/gsa/wiki/index.php/The_Genome_Analysis_Toolkit).

The software SAMtools [7] was used to determine sequence read depths observed in windows of one kilobase over the whole genome and candidate deletions and duplications were called using these depths. Furthermore the paired read mapping distances as well as strands were used to detect structural variations in relation to the reference assembly and in relation to the control pool.

Digital Droplet PCR (ddPCR)

The ddPCR reaction mixtures consisted of 11 µl 2×ddPCR Supermix for probes (Bio-Rad), 1.1 µl of the primer/probe mix for one of the deletion assays and 1.1 ul of the RNAsc P reference gene primer/probe mix (900 nM final concentration of each primer, 250 nM of probe) and 1 µl of sample DNA (concentration 20 ng/µl) in a final volume of 22 µl (see Table 1 for primer and probe sequences). 20 µl of reaction mixture was loaded into a disposable plastic cartridge (DG8, Bio-Rad) together with 70 µl of droplet generation oil (DG oil, Bio-Rad) and placed in the QX100 droplet generator (Bio-Rad). The droplets generated from each sample were then transferred to a 96-well Twin Tec semi-skirted PCR plate (Eppendorf, Germany) which was heat-sealed with Easy Pierce Foil (Thermo).

TABLE 1

Sequences of primers and probes used in digital droplet PCR to genotype deletions at the Equine SHOX locus

| Name | Target | Type | Sequence* | SEQ ID NO | 5'-modification | 3'-modification |
|---|---|---|---|---|---|---|
| EqD1_F | Deletion 1 | primer | TCCCCGRGTGTGGAAAGTTA | 1 | None | None |
| EqD1_R | Deletion 1 | primer | CCACAAAGCACATCCGTTTA | 2 | None | None |
| EqD1_probe | Deletion 1 | probe | ACGGGAAGGAGGGGGCCC | 3 | FAM | MGB |
| EqD2_F | Deletion 2 | primer | CCMGCTTTTGTCCCTTAAAC | 4 | None | None |
| EqD2_R | Deletion 2 | primer | TCCAGGCGATTTCCAACTAA | 5 | None | None |
| EqD2_probe | Deletion 2 | probe | CCAGCTCTGGGCTCGGCTCC | 6 | FAM | MGB |
| Eq_RNAseP_F | RNAse P | primer | GTTCCAAGCTCCGGCTAAG | 7 | None | None |
| Eq_RNAseP_R | RNAse P | primer | GGAGGTGGGTTCCCAGAG | 8 | None | None |
| Eq_RNAseP_probe | RNAse P | probe | TCTGCCCTCGCGCGGAGC | 9 | VIC | MGB |

*Non-standard bases correspond to nucleic acid ambiguity codes and indicate positions where mixed bases have been incorporated in primers PCR amplification was carried out on a T1000 Touch thermal cycler (Bio-Rad) using a thermal profile beginning at 95° C. for 10 min, followed by 40 cycles of 94° C. for 30 s and 60° C. for 60 s, 1 cycle of 98° C. for 10 min, and ending at 4° C. After amplification, the plate was loaded on the droplet reader (Bio-Rad) and the droplets from each well of the plate were read automatically. ddPCR data were analyzed using the QuantaSoft analysis software (Bio-Rad).

Identification of the Mutations Causing Skeletal Atavism

To identify the mutation(s) causing skeletal atavism in Shetland ponnies whole genome resequencing of affected horses and controls were performed. DNA samples from six individual Swedish Shetland ponies diagnosed with skeletal atavism, and a pool of 22 unaffected control stallions were sequenced using Illumina Hi-seq technology with resulting average sequence depths of 7× (each affected individual) and 55× (control pool). After aligning the reads to the reference genome assembly EquCab2 [5] (http://www.ncbi.nlm.nih.gov/assembly/GCA_000002305.1/) using the software BWA [6]. SAMtools [7] was used to determine genome wide depth of coverage for each sequenced sample and GATK [8] to call polymorphisms and to determine genotypes in the samples and to estimate the allele frequencies in the pool.

Next single nucleotide polymorphisms (SNPs) were screened for where each affected horse was homozygous for the variant allele and where the reference allele frequency was 100% in the control pool. In total, 25 SNPs fulfilled this criterion, and 17 of these were located to a very fragmented unplaced scaffold that contains the short stature homeobox (SHOX) gene.

An analysis of the depth of sequence read coverage revealed two separate partially overlapping deletions estimated to be at least 116 Kb and 34 Kb, respectively (FIG. 1) and involved the genome assembly contigs listed in Table 2.

TABLE 2

Horse sequence contigs predicted to be part of the two identified deletions based on depth of sequence coverage from the six cases and the control pool

| ^ Scaffold accession | ^ Contig accession | * Predicted to be part of deletion(s) | SEQ ID NO |
|---|---|---|---|
| NW_001867655.1 | AAWR02042945.1 | D1 AND D2 | 10 |
| NW_001867655.1 | AAWR02042946.1 | D1 AND D2 | 11 |
| NW_001867655.1 | AAWR02042947.1 | D1 AND D2 | 12 |
| NW_001867655.1 | AAWR02042948.1 | D1 AND D2 | 13 |
| NW_001867655.1 | AAWR02042949.1 | D1 AND D2 | 14 |
| NW_001867655.1 | AAWR02042950.1 | D1 AND D2 | 15 |
| NW_001867655.1 | AAWR02042951.1 | D1 AND D2 | 16 |
| NW_001867655.1 | AAWR02042952.1 | D1 AND D2 | 17 |
| NW_001867655.1 | AAWR02042953.1 | D1 AND D2 | 18 |
| NW_001867655.1 | AAWR02042954.1 | D1 AND D2 | 19 |
| NW_001867655.1 | AAWR02042955.1 | D1 AND D2 | 20 |
| NW_001867655.1 | AAWR02042956.1 | D1 AND D2 | 21 |
| NW_001867655.1 | AAWR02042957.1 | D1 AND D2 | 22 |
| NW_001867655.1 | AAWR02042958.1 | D1 AND D2 | 23 |
| NW_001867655.1 | AAWR02042959.1 | D1 AND D2 | 24 |
| NW_001867655.1 | AAWR02042960.1 | D1 AND D2 | 25 |
| NW_001867655.1 | AAWR02042961.1 | D1 AND D2 | 26 |
| NW_001867655.1 | AAWR02042962.1 | D1 AND D2 | 27 |
| NW_001867655.1 | AAWR02042963.1 | D1 AND D2 | 28 |
| NW_001867655.1 | AAWR02042964.1 | D1 AND D2 | 29 |
| NW_001867655.1 | AAWR02042965.1 | D1 AND D2 | 30 |
| NW_001867655.1 | AAWR02042966.1 | D1 AND D2 | 31 |
| NW_001867655.1 | AAWR02042967.1 | D1 AND D2 | 32 |
| NW_001867655.1 | AAWR02042968.1 | D1 AND D2 | 33 |
| NW_001867655.1 | AAWR02042969.1 | D1 AND D2 | 34 |
| NW_001867655.1 | AAWR02042970.1 | D1 AND D2 | 35 |
| NW_001867655.1 | AAWR02042971.1 | D1 AND D2 | 36 |
| NW_001867655.1 | AAWR02042972.1 | D1 AND D2 | 37 |
| NW_001867655.1 | AAWR02042973.1 | D1 AND D2 | 38 |
| NW_001867655.1 | AAWR02042974.1 | D1 AND D2 | 39 |
| NW_001867655.1 | AAWR02042975.1 | D1 AND D2 | 40 |
| NW_001867655.1 | AAWR02042976.1 | D1 AND D2 | 41 |
| NW_001867655.1 | AAWR02042977.1 | D1 AND D2 | 42 |
| NW_001867655.1 | AAWR02042978.1 | D1 AND D2 | 43 |
| NW_001867655.1 | AAWR02042979.1 | D1 AND D2 | 44 |
| NW_001867655.1 | AAWR02042980.1 | D1 AND D2 | 45 |
| NW_001867655.1 | AAWR02042981.1 | D1 AND D2 | 46 |
| NW_001867655.1 | AAWR02042982.1 | D1 AND D2 | 47 |
| NW_001867655.1 | AAWR02042983.1 | D1 AND D2 | 48 |
| NW_001867655.1 | AAWR02042984.1 | D1 AND D2 | 49 |
| NW_001867655.1 | AAWR02042985.1 | D1 AND D2 | 50 |
| NW_001867655.1 | AAWR02042986.1 | D1 AND D2 | 51 |
| NW_001867655.1 | AAWR02042987.1 | D1 AND D2 | 52 |
| NW_001867655.1 | AAWR02042988.1 | D1 AND D2 | 53 |
| NW_001867655.1 | AAWR02042989.1 | D1 AND D2 | 54 |
| NW_001867655.1 | AAWR02042990.1 | D1 AND D2 | 55 |
| NW_001867655.1 | AAWR02042991.1 | D1 AND D2 | 56 |
| NW_001867655.1 | AAWR02042992.1 | D1 AND D2 | 57 |
| NW_001867655.1 | AAWR02042993.1 | D1 AND D2 | 58 |
| NW_001867809.1 | AAWR02043090.1 | D1 | 59 |
| NW_001867809.1 | AAWR02043091.1 | D1 | 60 |
| NW_001867809.1 | AAWR02043092.1 | D1 | 61 |
| NW_001867809.1 | AAWR02043093.1 | D1 | 62 |
| NW_001867809.1 | AAWR02043094.1 | D1 | 63 |
| NW_001867809.1 | AAWR02043095.1 | D1 | 64 |
| NW_001867809.1 | AAWR02043096.1 | D1 | 65 |
| NW_001867809.1 | AAWR02043097.1 | D1 | 66 |
| NW_001867809.1 | AAWR02043098.1 | D1 | 67 |
| NW_001867809.1 | AAWR02043099.1 | D1 | 68 |
| NW_001867809.1 | AAWR02043100.1 | D1 | 69 |
| NW_001867809.1 | AAWR02043101.1 | D1 | 70 |
| NW_001867809.1 | AAWR02043102.1 | D1 | 71 |
| NW_001867809.1 | AAWR02043103.1 | D1 | 72 |
| NW_001867809.1 | AAWR02043104.1 | D1 | 73 |
| NW_001869437.1 | AAWR02043982.1 | D1 | 74 |
| NW_001869437.1 | AAWR02043983.1 | D1 | 75 |
| NW_001869437.1 | AAWR02043984.1 | D1 | 76 |
| NW_001869437.1 | AAWR02043985.1 | D1 | 77 |
| NW_001869437.1 | AAWR02043986.1 | D1 | 78 |
| NW_001869437.1 | AAWR02043987.1 | D1 | 79 |
| NW_001870009.1 | AAWR02044192.1 | D1 | 80 |
| NW_001870009.1 | AAWR02044193.1 | D1 | 81 |
| NW_001870009.1 | AAWR02044194.1 | D1 | 82 |
| NW_001870009.1 | AAWR02044195.1 | D1 | 83 |
| NW_001870009.1 | AAWR02044196.1 | D1 | 84 |
| NW_001870009.1 | AAWR02044197.1 | D1 | 85 |
| NW_001873507.1 | AAWR02044981.1 | D1 | 86 |
| NW_001873507.1 | AAWR02044982.1 | D1 | 87 |
| NW_001873507.1 | AAWR02044983.1 | D1 | 88 |
| NW_001875146.1 | AAWR02045249.1 | D1 | 89 |
| NW_001875146.1 | AAWR02045250.1 | D1 | 90 |
| NW_001876884.1 | AAWR02045517.1 | D1 AND D2 | 91 |
| NW_001876884.1 | AAWR02045518.1 | D1 AND D2 | 92 |
| NW_001876884.1 | AAWR02045519.1 | D1 AND D2 | 93 |
| NW_001876884.1 | AAWR02045520.1 | D1 AND D2 | 94 |
| NW_001876884.1 | AAWR02045521.1 | D1 AND D2 | 95 |
| NW_001871185.1 | AAWR02049699.1 | D1 | 96 |
| NW_001869338.1 | AAWR02043946.1 | D1 AND D2 | 97 |
| NW_001869338.1 | AAWR02043947.1 | D1 AND D2 | 98 |
| NW_001869338.1 | AAWR02043948.1 | D1 AND D2 | 99 |
| NW_001869338.1 | AAWR02043949.1 | D1 AND D2 | 100 |
| NW_001869338.1 | AAWR02043950.1 | D1 AND D2 | 101 |
| NW_001869338.1 | AAWR02043951.1 | D1 AND D2 | 102 |
| NW_001869338.1 | AAWR02043952.1 | D1 AND D2 | 103 |
| NW_001869338.1 | AAWR02043953.1 | D1 AND D2 | 104 |
| NW_001867532.1 | AAWR02045716.1 | D1 AND D2 | 105 |
| NW_001867532.1 | AAWR02045717.1 | D1 AND D2 | 106 |
| NW_001867532.1 | AAWR02045718.1 | D1 AND D2 | 107 |
| NW_001867532.1 | AAWR02045719.1 | D1 AND D2 | 108 |
| NW_001873348.1 | AAWR02051849.1 | D1 AND D2 | 109 |
| NW_001873348.1 | AAWR02051850.1 | D1 AND D2 | 110 |

^ Scaffold and Contig accessions: Genbank accession numbers of the reference genome assembly contigs and Scaffolds.
* Deletion overlap: Presumed deletion(s) involving the contig.

It was not possible to determine the exact size of the two deletions with confidence using this approach due to the poor assembly of this region. The largest deletion (D1) spans over the entire coding sequence of SHOX while the other (D2) involves the region immediately downstream of the SHOX coding sequence (FIG. 1). SHOX has been mapped to the pseudo-autosomal region (PAR) of the X and Y-chromosomes in other mammals and it is very likely that it is located in the PAR region in horses as well. In humans, mutation and haploinsufficiency of SHOX are associated with idiopathic growth retardation [9,10].

Sequencing of Bacterial Artificial Chromosomes (BACs)

In order to obtain additional sequence information BACs whose ends (BAC-ends) had been previously sequenced as a part of the generation of the horse genome assembly (EquCab2) and that were predicted to reside in the Pseudo-autosomal region close to the SHOX gene were identified. 13 such BACs from the CHORI-241 BAC library (http://bacpac.chori.org/library.php?id=41) made from a Thoroughbred male horse (not carrying the deletions Del1 or Del2), available from the BACPAC resource at the Childrens Hospital Oakland Research Institute (http://bacpac.chori.or&equine241.htm) were identified.

TABLE 4

Sequenced BACs from SHOX region

| BAC | Size(bp) | #scaffolds | Min (bp) | Max (bp) |
|---|---|---|---|---|
| CH241-087.2_E10 | 154 201 | 1 | 154 201 | 154 201 |
| CH241-121_P22 | 218 546 | 1 | 218 546 | 218 546 |
| CH241-231_N3 | 191 296 | 1 | 191 296 | 191 296 |
| CH241-219B18 | 67 454 | 2 | 899 | 66 555 |

TABLE 4-continued

Sequenced BACs from SHOX region

| BAC | Size(bp) | #scaffolds | Min (bp) | Max (bp) |
|---|---|---|---|---|
| CH241-52P20 | 66 939 | 2 | 852 | 66 087 |
| CH241-288L23 | 186 195 | 7 | 886 | 57 130 |
| CH241-159K1 | 47 668 | 4 | 1 660 | 27 250 |
| CH241-050_P17 | 147 467 | 1 | 147 467 | 147 467 |
| CH241-194_E12 | 155 628 | 1 | 155 628 | 155 628 |
| CH241-291B18 | 107 104 | 3 | 23 331 | 45 533 |
| CH241-419P11 | 73 186 | 1 | 73 186 | 73 186 |
| CH241-442L16 | 58 892 | 1 | 58 892 | 58 892 |
| CH241-712C2 | 140 175 | 1 | 140 175 | 140 175 |
| CH241-503B2 | 11 519 | 1 | 11 519 | 11 519 |

DNA was prepared from the purchased BACs (Table 4) according to standard laboratory procedures and, for each BAC, purified BAC DNA was subjected to sequencing using the Pacific Biosciences DNA sequencing methodology which is capable of generating long sequencing reads. Following sequencing, generated sequencing reads were subjected to de-novo assembly whereby individual reads from each BAC were assembled together into one or more contigs. The resulting assembled contigs were subsequently used as templates for alignment of the short Illumina sequencing reads from Atavism individuals CG1, CG2, CG3, CG4, CG5 and CG6 as well as the DNA pool comprising normal horses. This alignment information was used to determine sequencing read depth in windows to identify BAC-contigs or parts thereof where depth of coverage was consistent with the genotyped of the Atavistic horses, ie. CG1, CG5 and CG6 are of genotype Del1/Del1 and will therefore entirely lack high confidence read alignments for BAC contig parts corresponding to Deletion 1. Individuals CG2, CG3 and CG4 (Genotype=Del1/Del2) will have approximately half the depth of coverage compared to the pool of DNA from normal horses in the BAC contig parts unique to Deletion 1 and entirely lack coverage in the parts shared between Deletion 1 and Deletion 2.

used digital droplet PCR (ddPCR) (Biorad) to genotype 39 Swedish Shetland ponies, 18 known carriers, 6 affected horses and 15 unaffected horses, for the two deletions (D1 and D2). The six affected horses were the same as used for sequencing and we confirmed that three of them were homozygous D1/D1 and three were heterozygous D1/D2 (Table 3).

TABLE 3

Results of digital PCR analysis of the SHOX locus in horses with or without skeletal atavism. Three alleles occur at this locus: WT = wild type, D1 = Deletion 1, D2 = Deletion 2

| | Genotype | | | | | | | |
|---|---|---|---|---|---|---|---|---|
| Horse[a] | Failed genotyping | WT/WT | WT/D1 | WT/D2 | D1/D1 | D1/D2 | D2/D2 | Total |
| Affected | 0 | 0 | 0 | 0 | 3 | 3 | 0 | 6 |
| Carrier | 4 | 2 | 8 | 3 | 0 | 0 | 1 | 18 |
| Unaffected | 1 | 12 | 2 | 0 | 0 | 0 | 0 | 15 |

[a]Affected horses show skeletal atavism, Carriers are heterozygous for a disease causing mutation while Unaffected may be homozygous wild type or heterozygous for a disease causing mutation.

It was possible to trace the inheritance of these alleles from known carriers to affected offspring. All but two known carriers for which genotypes could be determined were heterozygous for one of the deletions (WT/D1 or WT/D2). All unaffected horses carried at least one copy of the WT allele. Thus, it was concluded that skeletal atavism is caused by two different deletion alleles associated with the SHOX locus. Affected horses may be homozygous D1/D1, heterozygous D1/D2 or possibly homozygous D2/D2. We have observed one carrier with genotype D2/D2 and this individual is not reported as affected suggesting that the D2/D2 genotype may not be associated with skeletal atavism at least not in all individuals with this genotype.

CONCLUSION

In conclusion, two deletions in the SHOX gene causing skeletal atavism in horses have been identified. Methods for

TABLE 5

BAC sequences identified to contain Del1 and/or Del2 sequences

| BAC | Scaffold | Size (bp) | Comment | breakpoints between | Del1 parts | Del2 parts |
|---|---|---|---|---|---|---|
| 194E12 | 194E.scf012 | 155 628 | This scaffold comprises a breakpoint and part of Del1 | Normal/Del1 breakpoint found between 133300-133500 bp | bp 133300-end SEQ ID NO: 111 | No Del2 part |
| 50P17 | 50P17.scf06 | 147 467 | This scaffold comprises a breakpoint and part of Del1 | Normal/Del1 breakpoint found between 82200-82300 bp ? | bp 82200-end SEQ ID NO: 112 | No Del2 part |
| 291B18 | 291B18.scf718013 | 37 613 | This scaffold comprises a part of Del1 | | 1-37613 bp SEQ ID NO: 113 | No Del2 part |
| 291B18 | 291B18.scf014 | 44 786 | This scaffold comprises a part of Del1, a breakpoint, a part of Del2, and another breakpoint | Del1/Del2 breakpoint found between 5100-5500 bp, (5100-5400 bp rich in repeats*) Del2/normal breakpoint found between 25500-25700 bp | 1-5100 bp SEQ ID NO: 114 5100-25700 bp SEQ ID NO: 115 | 5100-25700 bp SEQ ID NO: 115 |
| 52P20 | 1698_contig | 66 087 | This scaffold comprises a part of Del2 and a breakpoint. From 53700 bp contaminated with vector. | Normal/Del2 breakpoint found between 37800-38000 bp | 37800-53700 bp SEQ ID NO: 116 | 37800-53700 bp SEQ ID NO: 116 |
| 712C2 | 712C2.scf702 | 140 175 | This scaffold comprises a part of Del2 and a breakpoint. | Del2/Normal breakpoint somewhere between 59400-59600 bp | 1-59600 SEQ ID NO: 117 | 1-59600 bp SEQ ID NO: 117 |

*The Del1/Del2 breakpoint was found in a region rich in repeats not making it possible to exactly define the position of the breakpoint.

Genotyping Using ddPCR

Among the six affected horses, three were homozygous D1/D1 and three were D1/D2 composite heterozygotes. We detecting the presence of these deletions can now be used to identify unaffected carriers of these mutations and use this information to avoid the risk that a mating will produce an affected offspring. In matings between two carriers 25% of the progeny are expected to show skeletal atavism. The deletions can be detected using digital PCR or quantitative PCR.

REFERENCES

1. J G Speed: A cause of malformation of the limbs of Shetland ponies with a note on its phylogenic significance. *The British Veterinary Journal* 1958:18-22.
2. W A Hermans: A hereditary anomaly in Shetland ponies. *Neth J vet Sci.* 1970, 3(1):55-63.
3. Shamis L D, Auer J: Complete ulnas and fibulas in a pony foal. *J Am Vet Med Assoc* 1985, 186:802-804.
4. Tyson R, Graham J P, Colahan P T, Berry C R: Skeletal atavism in a miniature horse. *Vet Radiol Ultrasound* 2004, 45:315-317.
5. Wade C M, Giulotto E, Sigurdsson S, Zoli M, Gnerre S, Imsland F, Lear T L, Adelson D L, Bailey E, Bellone R R, et al.: Genome sequence, comparative analysis, and population genetics of the domestic horse. *Science* 2009, 326:865-867.
6. Li H, Durbin R: Fast and accurate short read alignment with Burrows-Wheeler transform. *Bioinformatics* 2009, 25:1754-1760.
7. Li H, Handsaker B, Wysoker A, Fennell T, Ruan J, Homer N, Marth G, Abecasis G, Durbin R, Subgroup GPDP: The Sequence Alignment/Map format and SAMtools. *Bioinformatics* 2009, 25:2078-2079.
8. McKenna A, Hanna M, Banks E, Sivachenko A, Cibulskis K, Kernytsky A, Garimella K, Altshuler D, Gabriel S, Daly M, et al.: The Genome Analysis Toolkit: a MapReduce framework for analyzing next-generation DNA sequencing data. *Genome Res* 2010, 20:1297-1303.
9. Blaschke R J, Rappold G: The pseudoautosomal regions, SHOX and disease. *Curr Opin Genet Dev* 2006, 16:233-239.
10. Rosilio M, Huber-Lequesne C, Sapin H, Carel J C, Blum W F, Cormier-Daire V: Genotypes and phenotypes of children with SHOX deficiency in France. *J Clin Endocrinol Metab* 2012, 97:E1257-1265.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11286527B2). An electronic copy of the "Sequence Listing" will also be available from the USPTO upon request and payment of the fee set forth in 37 CFR 1.19(b)(3).

The invention claimed is:

1. A method for breeding a horse, said method comprising the steps,
(i) extracting DNA from a biological sample obtained from said horse,
(ii) determining in said DNA two copies SEQ ID NO: 18, and
(iii) breeding said horse.

2. The method according to claim 1, comprising the amplification of a nucleic acid segment by means of the polymerase chain reaction (PCR).

3. The method according to claim 1, comprising hybridizing a primer or primer pair under stringent conditions to the sequence SEQ ID NO: 18.

* * * * *